US00PP29375P2

(12) United States Plant Patent
Tanaka

(10) Patent No.: US PP29,375 P2
(45) Date of Patent: Jun. 12, 2018

(54) ***HYDRANGEA* PLANT NAMED 'KAZAN'**

(50) Latin Name: *Hydrangea macrophylla*
Varietal Denomination: Kazan

(71) Applicant: Shinsuke Tanaka, Yokkaichi (JP)

(72) Inventor: Shinsuke Tanaka, Yokkaichi (JP)

( * ) Notice: Subject to any disclaimer, the term of this patent is extended or adjusted under 35 U.S.C. 154(b) by 0 days. days.

(21) Appl. No.: 15/530,652

(22) Filed: Feb. 15, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

(56) References Cited

PUBLICATIONS

PLUTO Plant Variety Database Jan. 9, 2018. p. 1.*

* cited by examiner

*Primary Examiner* — Annette H Para
(74) *Attorney, Agent, or Firm* — Audrey Charles

(57) ABSTRACT

A new and distinct cultivar of *Hydrangea* plant named 'Kazan', characterized by its double-type, mophead, light pink-colored inflorescences, medium green-colored foliage, and vigorous, upright growth habit, is disclosed.

1 Drawing Sheet

Latin name of genus and species of plant claimed: *Hydrangea macrophylla.*
Variety denomination: 'Kazan'.

BACKGROUND OF THE INVENTION

The present invention relates to a new and distinct cultivar of *Hydrangea* plant botanically known as *Hydrangea macrophylla* and hereinafter referred to by the cultivar name 'Kazan'.

The new cultivar originated in a controlled breeding program in Yokkaichi, Japan during June 2010. The objective of the breeding program was the development of *Hydrangea* cultivars that have double-type florets and vigorous, upright growth habits.

The new *Hydrangea* cultivar is the result of cross-pollination. The female (seed) parent of the new cultivar is a proprietary *Hydrangea macrophylla* breeding selection coded 21-3, not patented, characterized by its double-type, lacecap, light pink-colored inflorescences, medium green-colored foliage, and vigorous, upright growth habit. The male (pollen) parent of the new cultivar is a proprietary *Hydrangea macrophylla* breeding selection coded 21-30, not patented, characterized by its single-type mophead, light pink-colored inflorescences, medium green-colored foliage, and vigorous, upright growth habit. The new cultivar was discovered and selected as a single flowering plant within the progeny of the above stated cross-pollination during June 2012 in a controlled environment in in Yokkaichi, Japan.

Asexual reproduction of the new cultivar by softwood cuttings since June 2012 in Yokkaichi, Japan and Irvington, Ala. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kazan' as a new and distinct cultivar of *Hydrangea* plant:

1. Double-type, mophead, light pink-colored inflorescences;
2. Medium green-colored foliage; and
3. Vigorous, upright growth habit.

Plants of the new cultivar differ from plants of the female parent primarily in having a mophead flower form and darker pink-colored inflorescences. Plants of the new cultivar differ from plants of the male parent primarily in having a double flower type.

Of the many commercially available *Hydrangea* cultivars, the most similar in comparison to the new cultivar is Double Delights 'Perfection', U.S. Plant Pat. No. 22,221. However, in comparison, plants of the new cultivar differ from plants of 'Perfection' in at least the following characteristics:

1. Plants of the new cultivar have a lighter inflorescence color than plants of 'Perfection';
2. Plants of the new cultivar have a petaloid and sepal apex different from plants of 'Perfection'; and
3. Plants of the new cultivar have densely pubescent pedicels unlike plants of 'Perfection'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Kazan'. The plants were approximately one-year old and were grown in one-gallon containers for approximately 7 months in a poly-covered greenhouse in West Chicago, Ill. Plants were given one pinch at transplant.

DETAILED BOTANICAL DESCRIPTION

Figure 1:
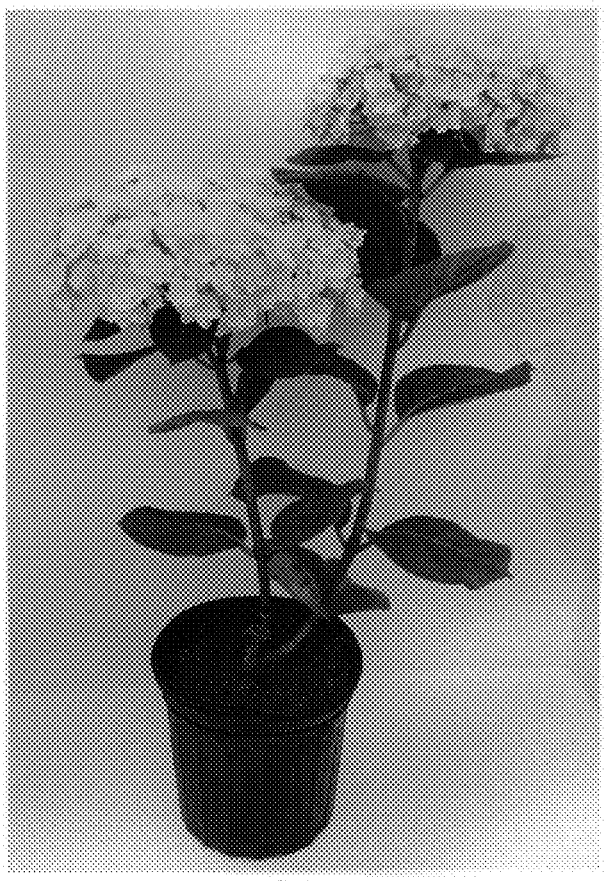
FIG. 1 illustrates a side view of the overall growth and flowering habit of 'Kazan'.
Figure 2:
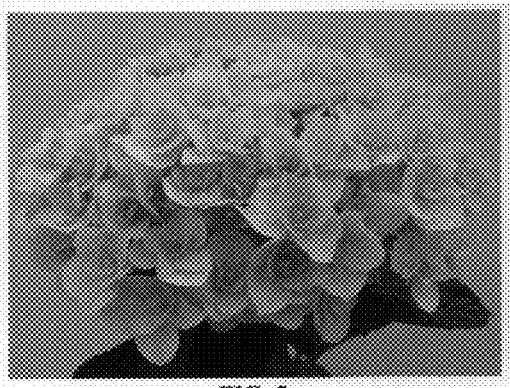
FIG. 2 illustrates an inflorescence with first-open florets of 'Kazan'.
Figure 3:
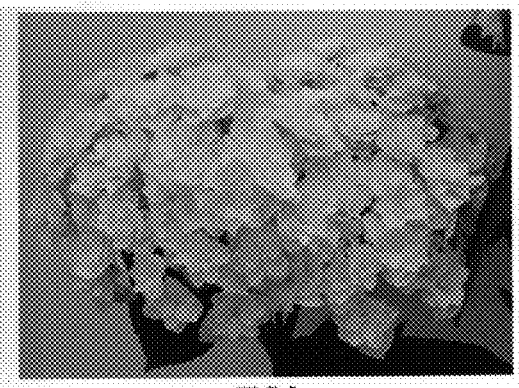
FIG. 3 illustrates an inflorescence with fully-open florets of 'Kazan'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2016 under natural light conditions in West Chicago, Ill.

The following descriptions and measurements describe approximately one-year old plants produced from softwood cuttings from stock plants and grown under conditions comparable to those used in commercial practice. The plants were grown in one-gallon containers for approximately 7 months in a poly-covered greenhouse in West Chicago, Ill. Plants were given one pinch at transplant. During winter months supplemental heat was provided to maintain temperatures above a minimum of 38° F. (3.3° C.). No supplemental lighting was provided. Measurements and numerical values represent averages of typical plants.

Botanical classification: *Hydrangea macrophylla* cultivar Kazan.

Parentage:

*Female parent.*—Proprietary *Hydrangea macrophylla* breeding selection coded 21-3, not patented.

*Male parent.*—Proprietary *Hydrangea macrophylla* breeding selection coded 21-30, not patented.

Propagation:

*Type cutting.*—Softwood cuttings.

*Time to initiate roots during the summer.*—Approximately 16 days.

*Time to produce a rooted cutting during the summer.*—Approximately 28 days.

*Time to initiate roots during the winter.*—Approximately 18 days.

*Time to produce a rooted cutting during the winter.*—Approximately 31 days.

*Root description.*—White to grey, medium thickness, fibrous.

*Rooting habit.*—Moderate branching and density.

Plant description:

*Commercial crop time.*—Approximately 30 to 34 weeks of cultivation from a rooted cutting followed by 9 to 11 weeks of forcing to finish in a 13.0 cm pot.

*Growth habit and general appearance.*—Deciduous shrub, mophead-type *Hydrangea*; vigorous, upright growth habit.

*Hardiness.*—USDA Zone 5 (−20° F. to −15° F.).

*Heat tolerance.*—Regularly tolerates temperatures as high as 38° C. in the summer.

*Size.*—Height from soil level to top of plant plane: Approximately 53.0 cm. Width: Approximately 40.0 cm.

*Branching habit.*—Freely branching. Pinching enhances branching. Quantity of lateral branches per plant: Approximately 2.

*Branch.*—Shape: Rounded. Strength: Strong. Length to base of inflorescence: Approximately 37.0 cm. Diameter: Approximately 1.0 cm. Length of central internode: Approximately 9.0 cm. Texture of young stem: Glabrous. Texture of mature stem: Glabrous, becomes woody with age. Color of young stem: 146C. Color of mature stem: 146C becoming 199A.

*Lenticels.*—Quantity per internode: Approximately 100. Shape: Round to elliptic. Size: Approximately 2.0 mm to 5.0 mm in length and approximately 1.0 mm in width. Color: 200A.

Foliage description:

*General description.*—Quantity of leaves per lateral branch: Approximately 8. Fragrance: None detected. Form: Simple. Arrangement: Opposite.

*Leaves.*—Aspect: Flat. Shape: Elliptic. Margin: Serrated. Apex: Acuminate. Base: Rounded. Venation pattern: Pinnate. Length of mature leaf: Approximately 13.5 cm. Width of mature leaf: Approximately 10.0 cm. Texture of upper and lower surfaces: Coriaceous, glabrous. Color of upper surface of young and mature foliage: 137A with venation of 145B to 145C. Color of lower surface of young and mature foliage: Closest to 138B with venation of 145B.

*Petiole.*—Length: Approximately 2.5 cm. Diameter: Approximately 5.0 mm. Texture: Glabrous. Color: 145B.

Flowering description:

*Flowering habit.*—Seasonal, May through August.

*Lastingness of individual inflorescence on the plant.*—Approximately 4 weeks.

Inflorescence description:

*General description.*—Type: Terminal compound corymb, globular, mophead in form, comprised of sterile flowers, lacks fertile flowers, persistent. Quantity per plant: Approximately 2. Fragrance: None detected. Aspect: Face upward. Height: Approximately 13.0 cm. Width: Approximately 25.0 cm. Quantity of sterile florets per inflorescence: Approximately 250.

*Peduncle.*—Strength: Strong. Shape: Rounded. Length: Approximately 5.0 cm. Diameter: Approximately 3.0 to 5.0 mm. Texture: Densely pubescent with appressed hairs. Color: 146C.

Floret description:

*General description.*—Type: Double, sterile, multiple whorls. Depth: Approximately 1.5 cm. Diameter: Approximately 4.0 cm.

*Bud just before opening.*—Shape: Globular. Diameter: Approximately 2.0 mm. Color: 144A.

*Petals/petaloids.*—Quantity: Approximately 12 to 13. Shape: Elliptic to obovate. Margin: Entire. Apex: Rounded. Base: Attenuate. Length of outermost: Approximately 1.5 cm. Width of outermost: Approximately 1.3 cm. Length of innermost: Approximately 8.0 mm. Width of innermost: Approximately 5.0 mm. Texture of upper and lower surfaces: Glabrous. Color of upper surface when first open: 145B to 145D. Color of lower surface when first open: NN155B tinted with 145D at base. Color of upper surface when fully open: 75C with outermost of NN155B having a faint overlay of 75C. Color of lower surface when fully open: 75D with outermost of NN155B having a faint overlay of 75D.

*Sepals.*—Quantity: Approximately 4. Arrangement: Cruciform. Shape: Elliptic. Margin: Entire. Apex:

Rounded. Base: Attenuate. Length: Approximately 2.0 cm. Width: Approximately 2.0 cm. Texture of upper and lower surfaces: Glabrous. Color of upper surface when first open: NN155B. Color of lower surface when first open: NN155B tinted with 145D at base. Color of upper surface when fully open: NN155B occasionally tinted with 145A. Color of lower surface when fully open: NN155B occasionally tinted with 145B.

*Pedicel.*—Strength: Strong, flexible. Aspect: Erect to approximately 45° from peduncle axis. Length: Approximately 2.7 cm. Diameter: Approximately 2.0 mm. Texture: Densely pubescent with appressed hairs. Color: Between 75A and 75B.

*Reproductive organs.*—Not observed.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'Kazan', substantially as herein illustrated and described.

* * * * *